United States Patent [19]

Rosati

[11] Patent Number: 4,923,864
[45] Date of Patent: May 8, 1990

[54] CERTAIN HETEROCYCLIC-HEXANAMIDES USEFUL FOR TREATING HYPERTENSION

[75] Inventor: Robert L. Rosati, Groton, Conn.

[73] Assignee: Pfizer Inc., New York, N.Y.

[21] Appl. No.: 261,878

[22] Filed: Oct. 24, 1988

Related U.S. Application Data

[63] Continuation-in-part of Ser. No. 132,373, Dec. 15, 1987, abandoned.

[51] Int. Cl.[5] .................. A61K 31/495; C07D 403/12; C07D 413/12; C07D 487/00
[52] U.S. Cl. .................................. 514/234.8; 544/116; 544/143; 544/144; 548/492; 548/494; 514/235.2; 514/415; 514/419
[58] Field of Search ....................... 544/143, 144, 116; 548/492, 494; 514/235.2, 415, 419, 234.8

[56] References Cited

U.S. PATENT DOCUMENTS 4,500,518 2/1985 Gordon et al. ..................... 514/2
4,820,691 4/1989 Patel ................................... 514/19

*Primary Examiner*—Alan L. Rotman
*Attorney, Agent, or Firm*—Peter C. Richardson; J. Trevor Lumb; James M. McManus

[57] ABSTRACT

Simple amides and derivatives thereof useful for inhibiting the angiotensinogen-cleaving action of the enzyme renin.

12 Claims, No Drawings

CERTAIN HETEROCYCLIC-HEXANAMIDES USEFUL FOR TREATING HYPERTENSION

CROSS REFERENCE TO RELATED APPLICATION

This application is a continuation-in-part of copending application Ser. No. 07/132,373 filed Dec. 15, 1987, now abandoned.

BACKGROUND OF THE INVENTION

This invention relates to novel simple amides and derivatives thereof useful as antihypertensive agents.

The proteolytic enzyme renin, which has a molecular weight of about 40,000, is produced in and secreted into the blood by the kidney. It is known to be active in vivo in cleaving the naturally-occurring plasma glycoprotein angiotensinogen, in the case of human angiotensinogen at the bond between the leucine (10th) and valine (11th) amino acid residues at the N-terminal end of the angiotensinogen:

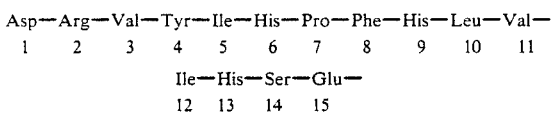

The circulating N-terminal decapeptide (angiotensin I) formed by the above cleaving action of renin is subsequently broken down by the body to an octapeptide known as angiotensin II. Angiotensin II is known to be a potent pressor substance, i.e., a substance that is capable of inducing a significant increase in blood pressure and is believed to act by causing the constriction of blood vessels and the release of the sodium-retaining hormone aldosterone from the adrenal gland. Thus, the renin-angiotensinogen system has been implicated as a causative factor in certain forms of hypertension and congestive heart failure.

One means of alleviating the adverse effects of the functioning of the renin-angiotensinogen system is the administration of a substance capable of inhibiting the angiotensinogen-cleaving action of renin. A number of such substances are known including antirenin antibodies, pepstatin and naturally-occurring phospholipid compounds. European Patent Application No. 45,665 (published Feb. 2, 1982) discloses a series of renin-inhibiting polypeptide derivatives of the formula X-Y-Pro-Phe-His-A-B-Z-W in which X may be hydrogen or an amino-protecting group, Y may be absent, B is a lipophilic amino acid residue, Z is an aromatic amino acid residue, W may be hydroxyl and A may be, inter alia,

with each of $R_1$ and $R_2$ being a lipophilic or aromatic side chain. According to the definitions set forth in this published patent application, it is not contemplated that either A or Z could be statine or that B could be lysine.

European Patent Application No. 77,028A (published Apr. 20, 1983) discloses a series of renin-inhibiting polypeptide compounds having a non-terminal statine or statine derivative residue. Included within this series are compounds having a phenylalanine-histidine-statine sequence.

European Patent Application No. 132,304A also discloses the use of statine containing polypeptides as renin-inhibiting antihypertensive agents, and European Patent Application No. 114,993A discloses polypeptides containing cyclostatine, useful as renin-inhibiting antihypertensive agents.

SUMMARY OF THE INVENTION

The simple amide renin inhibitors, useful as antihypertensive agents, are of the formula

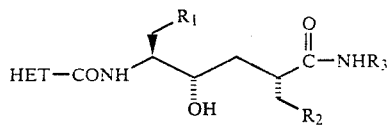

or a pharmaceutically acceptable salt thereof, wherein HET is

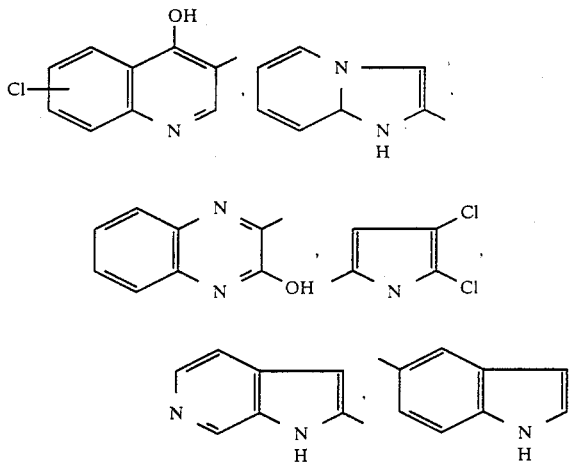

of a group of the formula

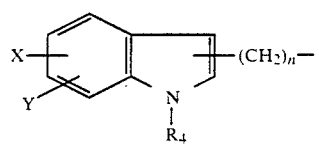

where X is hydrogen, $(C_1-C_3)$alkyl, $(C_1-C_3)$alkoxy, fluoro, chloro, bromo or cyano; Y is hydrogen, $(C_1-C_3)$alkyl, $(C_1-C_3)$alkoxy, fluoro or chloro; $R_4$ is hydrogen or $(C_1-C_3)$alkyl; n is an integer of 0 to 2; $R_1$ is $(C_6-C_8)$cycloalkyl or i-propyl; $R_2$ is $(C_3-C_5)$alkyl, phenyl, methylvinyl, dimethylvinyl, halovinyl, hydroxy$(C_1-C_3)$alkyl or amino$(C_1-C_4)$alkyl; and $R_3$ is $(C_1-C_6)$alkyl or morpholinoethyl.

Preferred within this group of compounds are those where HET is

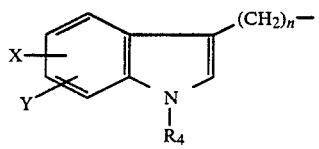

$R_1$ is cyclohexyl and $R_3$ is methyl. Especially preferred are the compounds where X is 5-chloro, Y is hydrogen, $R_4$ is hydrogen, n is 0 and $R_3$ is either i-propyl or —C(Cl)=CH$_2$, and where X and Y are hydrogen, $R_4$ is methyl, n is 0 and $R_2$ is i-propyl.

A second group of preferred compounds are those where HET is

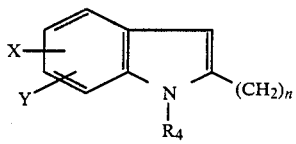

$R_1$ is cyclohexyl and $R_3$ is methyl. Especially preferred is the compound where X is 5-chloro, Y is hydrogen, $R_4$ is hydrogen, n is 0 and $R_2$ is —CH(OH)CH$_3$.

A third group of preferred compounds are those of the formula

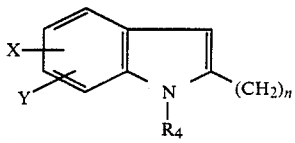

where $R_1$ is cyclohexyl and $R_2$ is methylvinyl. Especially preferred are the compounds where X is 5-chloro, Y is hydrogen, $R_4$ is hydrogen, n is 0, $R_2$ is —CH=CHCH$_3$ and $R_3$ is methyl and where X is 5-chloro, Y is hydrogen, $R_4$ is hydrogen, n is 0, $R_2$ is —CH=CHCH$_3$ and $R_3$ is morpholinoethyl.

The present invention also includes a method for treating hypertension in a mammal which comprised administering to said mammal an antihypertensive effective amount of the compounds of the present invention and a pharmaceutical composition comprised of the compounds of the present invention and a carrier.

As previously indicated, the present invention embraces pharmaceutically acceptable salts of the biologically active compounds. Such salts are those which are non-toxic at the dosages administered. Since compounds of the invention may contain basic groups, acid addition salts are possible. Pharmaceutically acceptable acid addition salts include e.g. the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts.

DETAILED DESCRIPTION OF THE INVENTION

The compounds of this invention exhibit antihypertensive activity in vivo in mammals, including humans. At least a substantial portion of this activity results from their ability to inhibit the cleavage of angiotensinogen by renin. Although we do not wish to be limited by the following theory of mechanism, it is likely that the mechanism of the renin-inhibiting activity of the compounds of the invention is their selective binding (as compared to angiotensinogen) to renin. The compounds of the invention exhibit an enzyme-inhibiting activity that is selective for renin. Because of their low molecular weights they exhibit favorable solubility characteristics in aqueous media and better absorbability, thus making oral administration feasible; and they can be synthesized at a commercially realistic cost. The compounds of the present invention are also useful against congestive heart failure.

The compounds of the invention may be prepared by methods familiar to those skilled in the art. The heterocyclic acids are coupled with the requisite amino lactone using coupling methods well known in the art for making amides. In this particular series of compounds the use of carbodiimides and N-hydroxybenzotriazole to form activated esters of the heterocyclic acids is preferred, although any of the many groups which are known to make activated esters can be employed. A second preferred means of coupling the requisite acid with the appropriate amino lactone is the use of diethyl cyanophosphate. This reagent is also well known for its use in the synthesis of amides.

Following the coupling of the appropriate heterocyclic acid and amino lactone, the lactone is treated with an amine resulting in the formation of the desired hydroxy-amide, having the necessary and desired stereochemistry to provide the antihypertensive activity which these compounds possess.

The starting reagents for the synthesis of these compounds are described herein or can be prepared by literature procedures. EPO application No. 86,305,995.2 [Publication 0212903(A2)] describes the preparation of polypeptides using an amino lactone similar to that described herein. Further, several of the heterocyclic acids are available commercially.

The ability of these compounds to act as antihypertensive agents by the inhibition of renin can be shown by the following in vitro assay:

Inhibition of the Angiotensinogen-Cleaving Activity of Renin In Vitro

Blood plasma was obtained from healthy laboratory personnel, pooled and stored frozen until required. Before use, a quantity of this plasma was defrosted and centrifuged, and the supernatant mixed with protease inhibitors and buffered to pH 7.4. Renin inhibitors were added at different levels to different aliquots of the plasma supernatant, and the resulting mixtures (310 lambda) incubated for three hours at 37° C. along with renin inhibitor-free control mixtures. After incubation, the mixtures were quenched in ice water and each assayed for angiotensin I using angiotensin I antibody. The production of angiotensin I in the presence of a renin inhibitor was compared to that produced in the absence of the inhibitor, and a percentage inhibition was calculated. Using data obtained from duplicate incubations at each of several different inhibitor concentrations, the inhibitor concentration in the incubation mixture required to produce a fifty percent inhibition of the angiotensinogen-cleaving activity of renin, i.e., the IC$_{50}$ of the inhibitor, was calculated for various different inhibitors.

The angiotensin I in the quenched incubation mixtures was assayed by means of a radioimmunoassay, using components of a renin radioimmunoassay kit supplied by Becton Dickinson and Co. (Orangeburg, N.Y.). This radioimmunoassay was based upon the one developed by Haber et al., *J. Clin. Endocrinol.*, 29, pp. 1349–1355 (1969).

The compounds of the present invention can be administered as antihypertensive agents by either the oral or parenteral routes of administration, with the former being preferred for reasons of patient convenience and comfort. In general, these antihypertensive compounds are normally administered orally in dosage ranging from about 0.1 mg to about 20 mg per kg of body weight per day and 0.1 mg to about 5 mg per kg of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups and the like. Such carriers included solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The compounds of the present invention are also useful in the diagnosis of hypertension and congestive heart failure.

The following examples illustrate the invention but are not to be construed as limiting the same.

EXAMPLE 1

2R,4S,5S-6-Cyclohexyl-5-(5'-chloroindol-2'-yl-carbonylamino)-4-hydroxy-2-(2'-chloro-2'-propenyl)-N-methylhexanamide (HET=5-chlorindol-2-yl; $R_1$=cyclohexyl; $R_2$=—C(Cl)=CH$_2$; and $R_3$=CH$_3$

1A.
2R,4S,5S-6-cyclohexyl-5-(5'-chloroindol-2'-yl-carbonylamino)-2-(2'-chloro-2'-propenyl)gamma-hexanolactone To 25 ml of methylene chloride at 0° C. was added 165.5 mg (0.5 mmol) of 2R,4S,5S-6-cyclohexyl-5-amino-2-(2'-chloro-2'-propenyl)-gamma-hexanolactone hydrochloride, 50.6 mg (0.5 mmol) of N-methyl morpholine, 97.8 mg (0.5 mmol) of 5-chloroindole-2-carboxylic acid, 67.5 mg (0.5 mmol) of N-hydroxybenzotriazole and 103 mg (0.5 mmol) of dicyclohexylcarbodiimide and the resulting reaction mixture stirred at room temperature overnight. The reaction mixture was filtered and the filtrate concentrated to dryness. The residue was redissolved in ethyl acetate, washed successively with water, a saturated sodium bicarbonate solution and brine and dried over magnesium sulfate. The solvent was removed and the residue, 280 mg, was chromatographed on silica gel using chloroform as the eluent to give 226 mg of the desired product.

1B.
2R,4S,5S-6-cyclohexyl-5-(5'-chloroindol-2'-yl-carbonylamino)-4-hydroxy-2-(2'-chloro-2'-propenyl)-N-methylhexanamide A solution of 226 mg of the product of Example 1A in 10 ml of methanol was saturated with methyl amine gas and the reaction mixture allowed to stand at room temperature for 1.5 hours. The reaction was concentrated to dryness and the residue triturated with ether to afford 155 mg of the desired product.

The NMR (CD$_3$OD) showed absorption at 2.7 (3H, s), 5.15 (2H, m) and 7.0–8.0 (4H, m) ppm.

EXAMPLE 2

Employing the procedure of Example 1A–1B, and starting with the appropriate starting reagents, the following compounds were prepared:

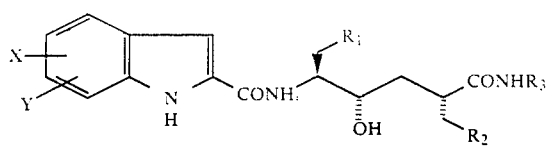

| X | Y | $R_1$ | $R_2$ | $R_3$ | NMR (60 MHz) delta (CD$_3$OD) |
|---|---|---|---|---|---|
| 5-Cl | H | C$_6$H$_{11}$ | i-C$_3$H- | CH$_3$ | 0.95 (9H, d, J=5 Hz), 2.7 (3H, s), 7.0–8.0 (4H, m) |

-continued

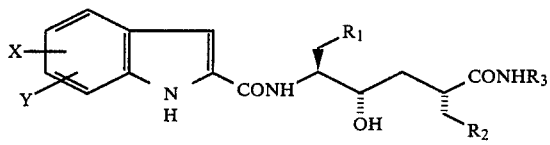

| X | Y | R₁ | R₂ | R₃ | NMR (60 MHz) delta (CD₃OD) |
|---|---|---|---|---|---|
| 5-Cl | H | $C_6H_{11}$ | −C(CH₃)=CH₂ | CH₃ | 1.65 (3H, s), 2.7 (3H, s), 4.65 (2H, m), 7.0–8.0 (4H, m) |
| 5-Cl | H | $C_6H_{11}$ | −CH=CH₂ | CH₃ | 2.7 (3H,s), 4.95 (2H, m), 7.0–8.0 (4H, m) |
| 5-Cl | H | $C_6H_{11}$ | −C(Cl)=CH₂ | CH₃ | 2.7 (3H, s), 5.15 (2H, m), 7.0–8.0 (4H, m) |
| 5-Cl | H | $C_6H_{11}$ | −C(Cl)=CH₂ | H | 5.15 (2H, m), 7.0–8.0 (4H, m) |
| 5-Cl | H | $i-C_3H_7$ | $i-C_3H_7$ | CH₃ | 0.95 (12H, m), 2.7 (3H, s), 7.0–8.0 (4H, m) |
| H | H | $C_6H_{11}$ | −C(Br)=CH₂ | CH₃ | 2.7 (3H, s), 5.5 (2H, m), 7.0–8.0 (5H, m) |
| 5-Cl | H | $C_6H_{11}$ | −CH=CH(CH₂N₃) | CH₃ | 2.7 (3H, s), 7.0–8.0 (4H, m) |
| 5-Cl | H | $C_6H_{11}$ | −CH(OH)−CH₃ | CH₃ | 1.1 (3H, d, J=5 Hz), 2.7 (3H, s), 7.0–8.0 (4H, m) |
| 5-Cl | H | $C_6H_{11}$ | −CH=CH−Cl | CH₃ | 2.7 (2H, m), 5.6–6.7 (2H, m) 7.0–8.0 (4H, m) |
| 5-Cl | H | $C_6H_{11}$ | CH=C(CH₃)₂ | CH₃ | 1.8 (6H, br s), 2.7 (3H, s), 7.0–8.0 (4H, m) |
| 3-Cl | H | $C_6H_{11}$ | $i-C_3H_7$ | CH₃ | 0.95 (6H, d, J=5 Hz), 2.7 (3H, s) |
| 5-Cl | H | $C_6H_{11}$ | −C(Br)=CH₂ | CH₃ | 2.7 (3H, s), 5.5 (2H, m), 7.0–8.0 (4H, m) |
| 5-Cl | H | $C_6H_{11}$ | $i-C_3H_7$ | CH₃ | 0.95 (6H, d, J=5 Hz), 2.4 (3H, s), 2.7 (3H, s), 7.0–8.0 (4H, m) |
| 5-Cl | H | $C_6H_{11}$ | CH₂CH(CH₃)C₂H₅ | CH₃ | 0.95 (12H, m), 2.7 (3H, s), 7.0–8.0 (4H, m) |
| 5-Cl | H | $C_6H_{11}$ | −CH=CH₂ | H | 2.7 (3H, s), 4.95 (2H, m), 7.0–8.0 (4H, m) |
| 5-Cl | H | $C_6H_{11}$ | −C₆H₅ | CH₃ | 2.7 (3H, s), 7.0–8.0 (9H, m) |
| H | H | $C_6H_{11}$ | $i-C_3H_7$ | CH₃ | 0.95 (6H, d, J=5 Hz), 2.7 (3H, s), 7.0–8.0 (5H, m) |
| 5-F | H | $C_6H_{11}$ | $i-C_3H_7$ | CH₃ | 0.95 (6H, d, J=5 Hz), 2.7 (3H, s), 7.0–8.0 (4H, m) |
| H | H | $C_6H_{11}$ | −CH=CH₂ | CH₃ | 2.7 (3H,s), 4.95 (2H, m), 7.0–8.0 (5H, m) |

-continued

[Structure: indole with X, Y substituents, N-H, connected to CONH-CH(R1)-CH(OH)-CH2-CH(R2)-CONHR3]

| X | Y | R₁ | R₂ | R₃ | NMR (60 MHz) delta (CD₃OD) |
|---|---|---|---|---|---|
| 5-Cl | H | C₆H₁₁ | —CH=CHCl | —(CH₂)₂N(morpholine) | 2.6 (6H, m), 5.15 (2H, m), 6.9–7.7 (4H, m) |
| 5-Cl | H | C₆H₁₁ | —CH=CHCH₃ | CH₃ | 1.6 (3H, m), 2.7 (3H, s), 6.9–7.7 (4H, m) |
| 5-Cl | H | C₆H₁₁ | —CH=CHCH₃ | —(CH₂)₂N(morpholine) | 1.6 (3H, m), 2.6 (6H, m), 5.3–5.7 (2H, m) |
| 5-Cl | H | C₆H₁₁ | i-C₃H₇ | —(CH₂)₂N(morpholine) | 0.95 (6H, d, J=5 Hz), 2.7 (3H, s), 6.9–7.7 (4H, m) |
| 5-Cl | H | C₆H₁₁ | —C(Cl)=CH₂ | —(CH₂)₂N(morpholine) | 2.6 (6H, m), 5.15 (2H, m), 5.9–7.7 (4H, m) |

EXAMPLE 3

2R,4S,5S-6-Cyclohexyl-5-(5'-chloroindol-3'-yl-carbonylamino)-4-hydroxy-2-(2'-methylpropyl)-N-methylhexanamide (HET=5-chlorindol-3-yl; R₁=cyclohexyl; R₂=-i-propyl; and R₃=CH₃

3A.

2R,4S,5S-6-cyclohexyl-5-(5'-chloroindol-3'-yl-carbonylamino)-2-(2'-methylpropyl)-gamma-hexanolactone To 10 ml of methylene chloride at 0° C. was added 20 mg (0.1 mmol) of 5-chloroindole-3-carboxylic acid, 30 mg (0.1 mmol) of 2R,4S,5S-6-cyclohexyl-5-amino-2-(2'-methylpropyl)-gamma-hexanolactone hydrochloride, 15 μl (0.1 mmol) of diethyl cyanophosphate and 42 μl (0.3 mmol) of triethylamine. Dimethylformamide (1 ml) was added and the reaction mixture allowed to stir at room temperature overnight. The reaction was concentrated to dryness and redissolved in ethyl acetate which was washed successively with water (2x), a saturated sodium bicarbonate solution (2x) and a brine solution. The solution was dried over sodium sulfate and concentrated to an oil, 51 mg.

3B.

2R,4S,5S-6-cyclohexyl-5-(5'-chloroindol-3'-yl-carbonylamino)-4-hydroxy-2-(2'-methylpropyl)-N-methylhexanamide A solution of the product of Example 3A in 10 ml of methanol was saturated with methyl amine at room temperature and the resulting reaction mixture was stirred at room temperature for 2 hours. The reaction was evaporated to dryness giving 61 mg of a foam which was chromatographed on silica gel using methanol-chloroform as the eluent. The fractions containing the product were combined and concentrated to give 14 mg of the desired product.

The NMR (CD₃OD) showed absorption at 0.95 (6H, d, J=5 Hz), 2.7 (3H, s) and 7.0–8.0 (4H, m) ppm.

EXAMPLE 4

Using the procedure of Example 3A–3B, and starting with the requisite starting reagents, the following compounds were prepared:

[Structure: indole with X, Y, N-R4 substituents, 3-position connected to CONH-CH(R1)-CH(OH)-CH2-CH(R2)-CONHR3]

| X | Y | R₁ | R₂ | R₃ | R₄ | NMR (60 MHz) delta (CD₃OD) |
|---|---|---|---|---|---|---|
| H | H | C₆H₁₁ | i-C₃H₇ | CH₃ | H | 0.95 (6H, d, J=5 Hz), 2.7 (3H, s), 7.0–8.0 (5H, m) |
| 7-CH₃ | H | C₆H₁₁ | i-C₃H₇ | CH₃ | H | 0.95 (6H, d, J=5 Hz), 2.7 (3H, s), 2.4 (3H, s), 6.8–8.0 (4H, m) |
| 5-Cl | H | C₆H₁₁ | i-C₃H₇ | CH₃ | H | 0.95 (6H, d, J=5 Hz), 2.7 (3H, s), 7.0–8.0 (4H, m) |
| 5-Cl | H | C₆H₁₁ | —C(Cl)=CH₂ | CH₃ | H | 2.7 (3H, s) 5.15 (2H, m), 7.0–8.0 (4H, m) |

-continued

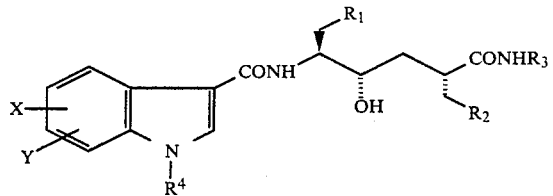

| X | Y | R₁ | R₂ | R₃ | R₄ | NMR (60 MHz) delta (CD₃OD) |
|---|---|---|---|---|---|---|
| H | H | $C_6H_{11}$ | $i$-$C_3H_7$ | $CH_3$ | $CH_3$ | 0.95 (6H, d, J=5 Hz), 2.7 (3H, s), 3.7 (3H, s), 7.0–8.0 (4H, m) |
| 5-CN | H | $C_6H_{11}$ | $i$-$C_3H_7$ | $CH_3$ | H | 0.95 (6H, d, J=5 Hz), 2.7 (3H, s), 7.0–8.0 (4H, m) |

EXAMPLE 5

2R,4S,5S-6-Cyclohexyl-5-(5'-bromoindol-3'-yl-acetylamino)-4-hydroxy-2-(2'-methylpropyl)-N-methylhexanamide (HET=5-bromoindol-3-yl-methyl; R₁=cyclohexyl; R₂=i-propyl; R₃=CH₃

5A.

2R,4S,5S-6-cyclohexyl-5-(5'-bromoindol-3'-yl-acetylamino)-2-(2'-methylpropyl)-gamma-hexanolactone To 10 ml of methylene chloride and 0.3 ml of dimethylformamide at 0° C. was added 30 mg (0.1 mmol) of 2R,4S,5S-6-cyclohexyl-5-amino-2-(2'-methylpropyl)-gamma-hexanolactone hydrochloride, 25 mg (0.1 mmol) of 5-bromoindole-3-acetic acid, 21 mg (0.1 mmol) of dicyclohexylcarbodiimide, 14 mg (0.1 mmol) of N-hydroxybenzotriazole and 11 μl (0.1 mmol) of N-methylmorpholine and the reaction mixture allowed to stir overnight at room temperature. The reaction was filtered and the filtrate evaporated to dryness. The residue was redissolved in ethyl acetate which was washed successively with water, a saturated sodium bicarbonate solution and a brine solution, and dried over sodium sulfate. The solvent was removed in vacuo and the residue, 54 mg, flash chromatographed on silica gel using 3% acetone as the eluent, 28 mg.

5B.

2R,4S,5S-6-cyclohexyl-5-(5'-bromoindol-3'-yl-acetylamino)-4-hydroxy-2-(2'-methylpropyl)-N-methylhexanamide A methanol (10 ml) solution containing 28 mg of the product of Example 5A was saturated with methyl amine at room temperature and allowed to stir for 2 hours. The reaction was evaporated to dryness and the residue triturated with hexane to give 30 mg of the desired product.

The NMR (CD₃OD) showed absorption at 0.95 (6H, d, J=5 Hz), 2.7 (3H, s) and 7.0–8.0 (4H, m) ppm.

EXAMPLE 6

Employing the procedure of Example 5A–5B, and using the appropriate starting materials, the following compounds were prepared:

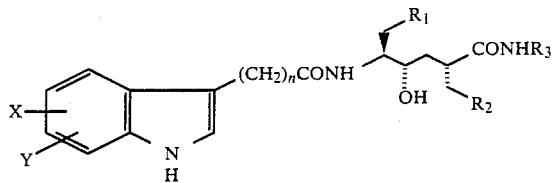

| X | Y | n | R₁ | R₂ | R₃ | NMR (60 MHz) delta (CD₃OD) |
|---|---|---|---|---|---|---|
| 5-$CH_3$ | H | 1 | $C_6H_{11}$ | $i$-$C_3H_7$ | $CH_3$ | 0.95 (6H, d, J=5 Hz), 2.7 (3H, s), 2.4 (3H, s), 7.0–8.0 (4H, m) |
| 5-Br | H | 1 | $C_6H_{11}$ | $i$-$C_3H_7$ | $CH_3$ | 0.95 (6H, d, J=5 Hz), 2.7 (3H, s), 7.0–8.0 (4H, s) |
| H | H | 2 | $C_6H_{11}$ | $i$-$C_3H_7$ | $CH_3$ | 0.95 (6H, d, J=5 Hz), 2.7 (3H, s) |
| H | H | 1 | $C_6H_{11}$ | $i$-$C_3H_7$ | $CH_3$ | 0.95 (6H, d, J=5 Hz), 2.7 (3H, s) |

EXAMPLE 7

2R,4S,5S-6-Cyclohexyl-5-(6'-azaindol-2'-yl-carbonylamino)-4-hydroxy-2-(2'-methylpropyl)-N-methylhexanamide (HET=6-azaindol-2-yl; R₁=cyclohexyl; R₂=i-propyl; R₃=CH₃

7A.

2R,4S,5S-6-cyclohexyl-5-(6'-azaindol-2'-yl-carbonylamino)-2-(2'-methylpropyl)-gamma-hexanolactone To 10 ml of methylene chloride and 0.5 ml of dimethylformamide at 0° C. was added 37 mg (0.1 mmol) of 2R,4S,5S-6-cyclohexyl-5-amino-2-(2'-methylpropyl)-gamma-hexanolactone hydrochloride, 33 mg (0.2 mmol) of 6-azaindole-2-carboxylic acid, 25 mg (0.1 mmol) of dicyclohexylcarbodiimide, 17 mg (0.1 mmol) of N-hydroxybenzotriazole and 20 μl (0.1 mmol) of N-methylmorpholine, and the reaction allowed to stir at room temperature for 48 hours. The reaction was filtered, washed with water and a saturated sodium bicarbonate solution and dried over sodium sulfate. Evaporation of the solvent gave 55 mg of the desired product.

7B.

2R,4S,5S-6-cyclohexyl-5-(6'-azaindol-2'-yl-carbonylamino)-4-hydroxy-2-(2'-methylpropyl)-N-methylhexanamide A solution of 55 mg of the product of Example 7A in 10 ml of methanol was saturated with methyl amine at room temperature and the reaction allowed to stand for 2 hours. The solvent was removed in vacuo and the residue chromatographed on silica gel using methanol-chloroform as the eluent to give 9.7 mg of product.

The NMR spectrum (CD₃OD) showed absorption at 0.95 (6H, d, J=5 Hz) and 2.7 (3H, s) ppm.

EXAMPLE 8

Employing the procedure of Example 7A–7B, and starting with the appropriate starting materials, the following compounds were prepared:

| HET | NMR (60 MHz) delta (CD₃OD) |
|---|---|
| 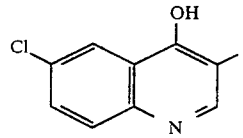 | 0.95 (6H, d, J=5 Hz), 2.7 (3H, s), 7.0–8.0 (4H, m) |
| 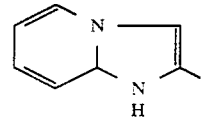 | 0.95 (6H, d, J=5 Hz), 2.7 (3H, s) |
| 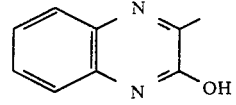 | 0.95 (6H, d, J=5 Hz), 2.7 (3H, s) |
| 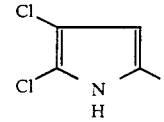 | 0.95 (6H, d, J=5 Hz), 2.7 (3H, s) |
| 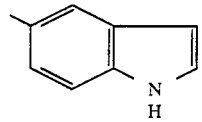 | 0.95 (6H, d, J=5 Hz), 2.7 (3H, s) |

EXAMPLE 9

2R,4S,5S-6-Cyclohexyl-5-(indol-2′-yl-carbonylamino)-4-hydroxy-2-(4′-aminobutyl)-N-methylhexanamide (HET=indol-2-yl; $R_1$=cyclohexyl; $R_2$=(CH$_2$)$_4$NH$_2$; $R_3$=CH$_3$)

A mixture of 75 mg of 2R,4S,5S-6-cyclohexyl-5-(5′-chloroindol-2′-ylcarbonylamino)-4-hydroxy-2-(4′-azido-2′-butenyl)-N-methylhexanamide, 35 mg of palladium-on-charcoal and 5 ml of acetic acid in 5 ml of methanol was shaken in a hydrogen atmosphere at 50 psi for 6 hours. An additional 35 mg of catalyst was added and the reduction continued overnight. The catalyst was filtered and the filtrate concentrated in vacuo to give 66 mg of product. The residue was triturated with ether and filtered, 50 mg.

The NMR (CD₃OD) spectrum showed absorption at 2.7 (3H, s) and 7.0–8.0 (5H, m) ppm.

PREPARATION A 2R,4S,5S-6-Cyclohexyl-5-(t-butoxycarbonylamino)-2-(2′-chloro-2′-propenyl)-gamma-hexanolactone To a tetrahydrofuran solution containing 37.5 mmol of lithium diethylamide at −70° C. (prepared from 23.4 ml of 1.6M butyl lithium hexane and 4.26 g of diethylamine in 50 ml of dry tetrahydrofuran) was added dropwise a solution of 4.67 g (15 mmol) of 4S,5S-6-cyclohexyl-5-(t-butoxycarbonylamino)-gamma hexanolactone in 25 ml of tetrahydrofuran. After 30 minutes at −78° C. a solution of 3.64 g (16 mmol) of 2-chloro-3-iodopropene in 25 ml of tetrahydrofuran was added dropwise at −70° C. After 2 hours the reaction mixture was quenched with 10 ml of a saturated ammonium chloride solution added dropwise at −78° C., and the resulting mixture allowed to warm to room temperature. The solvent was removed in vacuo and the residue extracted with diethyl ether. The ether solution was washed with a 10% citric acid solution, a saturated sodium bicarbonate solution and a brine solution. The ether solution was then dried over magnesium sulfate and concentrated to give 6.83 g of an oil, which was chromatographed on silica gel using ethyl acetate-hexane as the eluent. The fractions containing the product were combined and concentrated to give 2.38 g of the desired product.

The NMR spectrum (CDCl₃) showed absorption at 1.4 (9H, s) ppm.

PREPARATION B

Employing the procedure of Preparation A, and using the appropriate starting reagents, the following intermediates were synthesized:

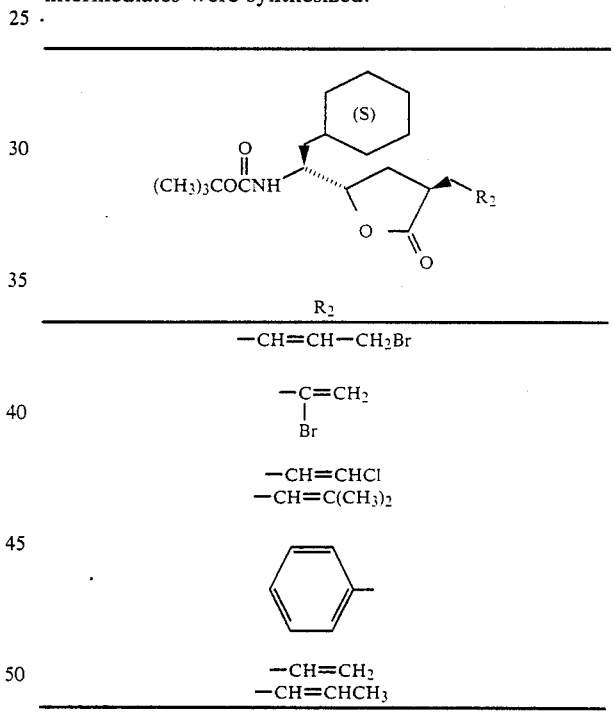

| $R_2$ |
|---|
| —CH=CH—CH$_2$Br |
| —C(Br)=CH$_2$ |
| —CH=CHCl |
| —CH=C(CH$_3$)$_2$ |
| —C$_6$H$_5$ |
| —CH=CH$_2$ |
| —CH=CHCH$_3$ |

PREPARATION C 2R,4S,5S-6-Cyclohexyl-5-(t-butoxycarbonylamino)-2-(4-azido-2-butenyl)-gamma-hexanolactone A solution of 710 mg (1.6 mmol) of 2R,4S,5S-6-cyclohexyl-5-(t-butoxycarbonylamino)-2-(4′-bromo-2′-butenyl)-gamma-hexanolactone and 986 mg (15.2 mmol) of sodium azide in 75 ml of dimethylsulfoxide-water (2:1; v:v) was allowed to stir overnight at room temperature. The reaction was poured into 500 ml of water and the product extracted with ethyl acetate. The extracts were combined and washed successively with water and a brine solution, and were dried over magnesium sulfate. The solvent was removed in vacuo to give 73 mg of the desired product.

PREPARATION D

2R,4S,5S-6-Cyclohexyl-5-(t-butoxycarbonylamino)-2-(2'-hydroxypropyl)-gamma-hexanolactone A solution of 100 mg (0.27 mmol) of 2R,4S,5S-6-cyclohexyl-5-(t-butoxycarbonylamino)-2-(2'-methyl-2'-propenyl)-gamma-hexanolactone in 15 ml of methylene chloride was saturated with ozone at −78° C. until there was a permanent blue coloration. The reaction mixture was allowed to stand for 30 minutes at −78° C. and was then purged of excess ozone at −78° C. with a rapid stream of nitrogen. Tetrabutyl ammonium borohydride (140 mg, 0.54 mmol) was added at −78° C. and the reaction mixture was allowed to stand at 0° C. for 2 days. An additional 140 mg of borohydride was added and the reaction mixture allowed to stand overnight at room temperature. The solution was washed with water and a brine solution, dried over sodium sulfate and evaporated to give 250 mg of crude product. Flash chromatographing using chloroform-methanol (99:1; v:v) afforded 45 mg of the desired intermediate.

The NMR (CDCl$_3$) spectrum showed absorption at 1.4 (9H, s) ppm.

PREPARATION E

2R,4S,5S-6-Cyclohexyl-5-amino-2-(2'-chloro-2'-propenyl)-gamma-hexanolactone hydrochloride A solution of 385 mg (1 mmol) of 2R,4S,5S-6-cyclohexyl-5-(t-butoxycarbonylamino)-2-(2'-chloro-2'-propenyl)-gamma-hexanolactone in 10 ml of 4.7N hydrogen chloride in dioxane was allowed to stir for 2 hours at room temperature. The solvent was removed in vacuo to give 331 mg of the desired amine hydrochloride.

PREPARATION F

Using the procedure of Preparation E, and employing the intermediates of Preparations A, B and D, the following intermediates were prepared:

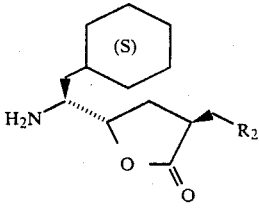

| $R_2$ |
|---|
| 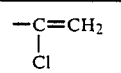 |
| 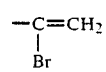 |
| —CH=CHCl |
| —CH=C(CH$_3$)$_2$ |
| 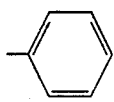 |
| —CH=CH$_2$ |

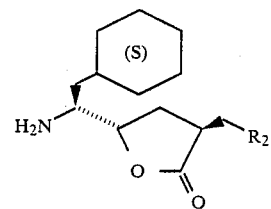

| $R_2$ |
|---|
| —CH—CH$_3$<br>\|<br>OH |
| —CH=CHCH$_3$ |

I claim:

1. A compound selected from those of the formula

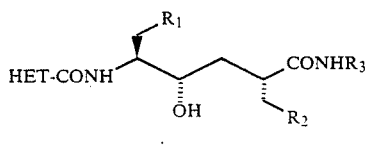

or a pharmaceutically acceptable salt thereof, wherein HET is

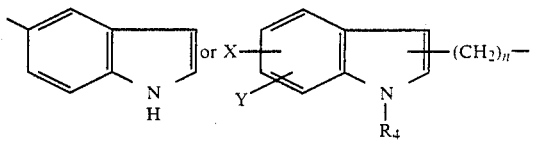

where X is hydrogen, (C$_1$-C$_3$)alkyl, (C$_1$-C$_3$)alkoxy, fluoro, chloro, bromo or cyano; Y is hydrogen, (C$_1$-C$_3$)alkyl, (C$_1$-C$_3$)alkoxy, fluoro or chloro; R$_4$ is hydrogen or (C$_1$-C$_3$)alkyl; n is an integer of 0 to 2; R$_1$ is (C$_6$-C$_8$)cycloalkyl or i-propyl; R$_2$ is (C$_3$-C$_5$)alkyl, phenyl, methylvinyl, dimethylvinyl, halovinyl, hydroxy(C$_1$-C$_3$)alkyl or amino(C$_1$-C$_4$)alkyl; and R$_3$ is (C$_1$-C$_6$)alkyl or morpholinoethyl.

2. A compound of claim 1, wherein HET is a group of the formula

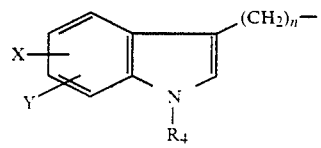

R$_1$ is cyclohexyl and R$_3$ is methyl.

3. The compound of claim 2, wherein X is 5-chloro, Y is hydrogen, R$_4$ is hydrogen, n is 0 and R$_2$ is i-propyl.

4. The compound of claim 2, wherein X and Y are each hydrogen, R$_4$ is methyl, n is 0 and R$_2$ is i-propyl.

5. A compound of claim 1, wherein HET is a group of the formula

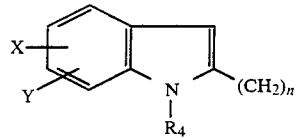

$R_1$ is cyclohexyl and $R_3$ is methyl.

6. The compound of claim 5, wherein X is 5-chloro, Y is hydrogen, $R_4$ is hydrogen, n is 0 and $R_2$ is —CH(OH)CH$_3$.

7. The compound of claim 2, wherein X is 5-chloro, Y is hydrogen, $R_4$ is hydrogen, n is 0 and $R_2$ is —C(Cl)=CH$_2$.

8. A compound of claim 1, wherein HET is a group of the formula

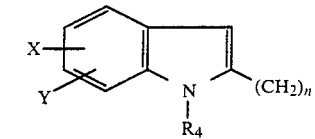

$R_1$ is cyclohexyl and $R_2$ is methylvinyl.

9. The compound of claim 8, wherein X is 5-chloro, Y is hydrogen, $R_4$ is hydrogen, n is 0, $R_2$ is —CH=CHCH$_3$ and $R_3$ is methyl.

10. The compound of claim 8, wherein X is 5-chloro, Y is hydrogen, $R_4$ is hydrogen, n is 0, $R_2$ is —CH=CHCH$_3$ and $R_3$ is morpholinoethyl.

11. A method of treating hypertension in a mammal which comprises administering to said mammal an antihypertensive effective amount of a compound according to claim 1.

12. A pharmaceutical composition comprising an antihypertensive effective amount of a compound according to claim 1 and a pharmaceutically acceptable diluent or carrier.

* * * * *